(12) United States Patent
Ghanem et al.

(10) Patent No.: US 8,620,414 B2
(45) Date of Patent: Dec. 31, 2013

(54) DETECTION OF T-WAVE ALTERNANS PHASE REVERSAL FOR ARRHYTHMIA PREDICTION AND SUDDEN CARDIAC DEATH RISK STRATIFICATION

(75) Inventors: Raja N. Ghanem, Edina, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 749 days.

(21) Appl. No.: 12/749,753

(22) Filed: Mar. 30, 2010

(65) Prior Publication Data
US 2011/0245700 A1    Oct. 6, 2011

(51) Int. Cl.
*A61B 5/0452* (2006.01)

(52) U.S. Cl.
USPC ........... 600/515; 600/508; 600/509; 600/516; 600/517; 600/518; 600/519

(58) Field of Classification Search
USPC .................................. 600/508–509, 515–519
See application file for complete search history.

(56) References Cited

U.S. PATENT DOCUMENTS

| | | | |
|---|---|---|---|
| 5,117,824 A | 6/1992 | Keimel et al. | |
| 5,312,441 A | 5/1994 | Mader et al. | |
| 6,393,316 B1 | 5/2002 | Gillberg et al. | |
| 6,823,213 B1 | 11/2004 | Norris et al. | |
| 6,915,156 B2 | 7/2005 | Christini | |
| 6,983,183 B2 | 1/2006 | Thiagarajan et al. | |
| 7,187,966 B2 * | 3/2007 | Kaiser et al. | 600/515 |
| 2002/0138106 A1 | 9/2002 | Christini et al. | |
| 2004/0002743 A1 | 1/2004 | Park et al. | |
| 2004/0186527 A1 | 9/2004 | Rouw et al. | |
| 2005/0234362 A1 | 10/2005 | Kaiser et al. | |
| 2006/0116592 A1 | 6/2006 | Zhou et al. | |
| 2006/0116596 A1 | 6/2006 | Zhou et al. | |
| 2007/0123787 A1 | 5/2007 | Kitajima et al. | |

FOREIGN PATENT DOCUMENTS

| | | |
|---|---|---|
| WO | 2007013911 A2 | 2/2007 |
| WO | 2009048845 A1 | 4/2009 |

OTHER PUBLICATIONS

P0034619.01 (PCT/US2011/027469) PCT Notification of Transmittal of the International Search Report and the Written Opinion of the International Searching Authority, Mailed Jun. 9, 2011, 12 pages.

* cited by examiner

*Primary Examiner* — Deborah Malamud
(74) *Attorney, Agent, or Firm* — Michael C. Soldner

(57) ABSTRACT

An implantable medical device and associated method for classifying a patient's risk for arrhythmias by sensing a cardiac electrogram (EGM) signal and selecting a first pair of T-wave signals and a second pair of T-wave signals. A first difference between the two T-wave signals of the first pair is compared to a second difference between the two T-wave signals of the second pair. A T-wave alternans phase reversal is detected in response to comparing the first difference and the second difference, and the patient's arrhythmia risk is classified in response to detecting the phase reversal.

9 Claims, 4 Drawing Sheets

DETECTION OF T-WAVE ALTERNANS PHASE REVERSAL FOR ARRHYTHMIA PREDICTION AND SUDDEN CARDIAC DEATH RISK STRATIFICATION

TECHNICAL FIELD

The disclosure relates generally to medical devices and, in particular, to a device and method for monitoring T-wave alternans in a patient.

BACKGROUND

T-wave alternans (TWA) is beat-to-beat alternation in the morphology, amplitude, and/or polarity of the T-wave, and can be observed on surface electrocardiogram (ECG) recordings. TWA has been recognized in a variety of clinical conditions, including acquired and congenital long QT syndrome and ischemic heart disease, and has been found to be associated with ventricular arrhythmias. TWA is considered an independent predictor for cardiac arrhythmias. Experimentally, TWA has been shown to be a precursor of ventricular tachycardia.

In past practice, TWA has been assessed from surface ECG recordings obtained in a clinical setting as an indication of the long-term risk for ventricular arrhythmias. A Fast Fourier Transform (FFT) method is used for frequency domain analysis of T-waves, and a Modified Moving Averaging (MMA) method is used for time domain analysis of T-waves. The low-amplitude changes in the T-wave signal during TWA, which is on the order of microvolts, requires complicated software to assess TWA from a surface ECG recording of typically 128 heart beats or more during exercise or high-rate atrial pacing when using the FFT method. A need remains for TWA assessment and monitoring in implantable medical devices for identifying patients at high risk for ventricular arrhythmias and sudden cardiac death.

DETAILED DESCRIPTION

Figure 1:
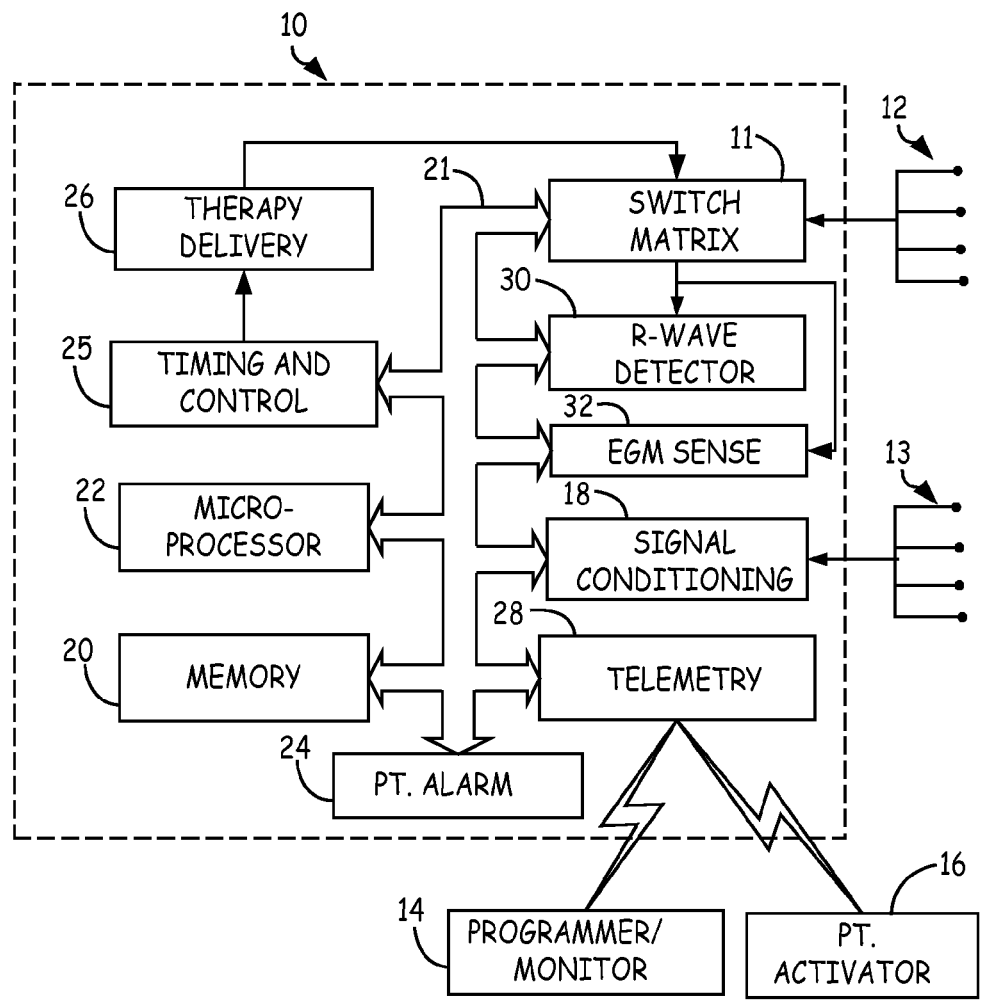
FIG. 1 is a functional block diagram of an IMD system that may be used for monitoring TWA.

In the following description, references are made to illustrative embodiments for carrying out the methods disclosed. It is understood that other embodiments may be utilized without departing from the scope of the disclosure. In some instances, for purposes of clarity, the same reference numbers my be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a functional block diagram of an IMD system that may be used for monitoring TWA. The system provides for dynamic monitoring of TWA in an ambulatory patient. The system includes IMD 10 and associated electrodes 12 for acquiring EGM signals. EGM signals are used by IMD 10 for assessing the cardiac rhythm for determining if and when a therapy is needed. IMD 10 further uses the acquired EGM signals for TWA assessment, as will be described herein.

IMD 10 may also be coupled to one or more physiological sensors 13, such as an activity sensor or hemodynamic sensors, such as blood pressure sensors. Physiological signals may be used for detecting cardiac events such as arrhythmias or hemodynamic events. Physiological signals may be used by IMD 10 for triggering certain device operations.

IMD 10 is adapted for bidirectional communication with an external programmer/monitor 14 via telemetry circuitry 28. Programmer/monitor 14 is used for programming operating parameters in IMD 10 and for uplinking data from IMD 10. In accordance with one embodiment, programmer/monitor 14 may be used by a clinician to initiate a TWA assessment. Alternatively, programmer/monitor 14 may be used to program parameters controlling an automated TWA assessment performed by IMD 10. A TWA report may be received by programmer/monitor 14 from IMD 10 including TWA data and/or TWA assessment results. In some embodiments, EGM data acquired by IMD 10 for use in TWA assessment may be transferred to programmer/monitor 14 for analysis by programmer/monitor 14 or another external computer system such as a remote patient management network. IMD 10 may also be adapted for communicating with a patient activator 16 which may be used by a patient or other caregiver to initiate a TWA assessment.

IMD 10 includes an R-wave detector 30, which receives EGM signals from electrodes 12 via switch matrix 11. R-wave detector 30 includes a sense amplifier having frequency response characteristics and beat-by-beat automatic adjusting sensitivity for accurate R-wave detection.

IMD 10 further includes an EGM sense amplifier 32 that may be used for acquiring EGM signals for specialized signal analyses. EGM sense amplifier 32 receives signals from electrodes 12 via switch matrix 11. EGM sense amplifier 32 provides a wider band of frequency response than R-wave detector 30 and a separately adjustable gain setting. EGM sense amplifier 32 may be embodied as an automatic gain control sense amplifier enabled for automatic gain adjustment responsive to the amplitude of sensed T-wave signals. EGM signal segments for use in specialized analyses, such as TWA assessment, may be extracted from EGM signals obtained by sense amplifier 32 based on relative timing from R-waves detected by R-wave detector 30. In particular, T-wave signal analysis can be performed to obtain T-wave measurements during a T-wave sensing window selected relative to an R-wave detection signal from R-wave detector 30.

Electrodes 12 may be located on leads extending from IMD 10 or may be leadless electrodes incorporated in or on the housing of IMD 10. R-wave detector 30 and EGM sense amplifier 32 receive signals from electrodes 12 via switch matrix 11. Optional switch matrix 11, under the control of microprocessor 22, is used for selecting which electrodes are coupled to R-wave detector 30 for reliable R-wave detection and which electrodes are coupled to EGM sense amplifier 32 for use in TWA assessment.

IMD 10 includes a signal conditioning module 18 for receiving EGM signals from EGM sense amplifier 32 and physiological signals from sensors 13. Signal conditioning module 18 includes sense amplifiers and may include other signal conditioning circuitry such as filters and an analog-todigital converter. Microprocessor 22 receives signals on system bus 21 from signal conditioning module 18 for detecting physiological events.

Memory 20 is provided for storing conditioned EGM signal output from conditioning module 18. In one embodiment, processing of EGM signals for assessing TWA is performed by IMD microprocessor 22. Microprocessor 22, controls IMD functions according to algorithms and operating parameters stored in memory 20. Microprocessor 22 may perform TWA assessment according to the methods to be described below. In response to TWA assessment results, microprocessor 22 may cause an alert signal to be generated by alarm circuitry 24. Additionally or alternatively, a therapy delivery module 26 may be signaled to deliver or withhold a therapy, or adjust therapy delivery parameters under the control of timing and control circuitry 25. Therapy delivery module 26 may be configured to deliver a cardiac pacing therapy, anti-tachycardia pacing therapies, arrhythmia therapies including cardioversion/defibrillation shock delivery, drug therapies, neurostimulation, or other cardiac therapies.

In various embodiments, control circuitry implemented for performing automated TWA assessment in IMD 10 may include application specific integrated circuit (ASIC), an electronic circuit, a processor (shared, dedicated, or group) and memory that execute one or more software or firmware programs, a combinational logic circuit, or other suitable components that provide the described functionality. The implementation of TWA assessment provided herein is not limited to a particular type of system architecture.

In other embodiments, EGM data acquired by IMD 10 for use in TWA assessment may be stored in memory 20 and downlinked to external programmer/monitor 14. All T-wave signal sample points acquired by the IMD may be stored for use in assessing TWA or only specified data points may be stored, such as every 30 ms or other sampling rate during the T-wave sensing window, if memory space is limited. Processing circuitry included in programmer/monitor 14 may then perform a TWA assessment according to programmed algorithms. Reports of TWA assessment results may be generated by either IMD 10 or external programmer/monitor 14, for display, printing or electronic storage such that the results are available for review by a clinician.

Figure 2:
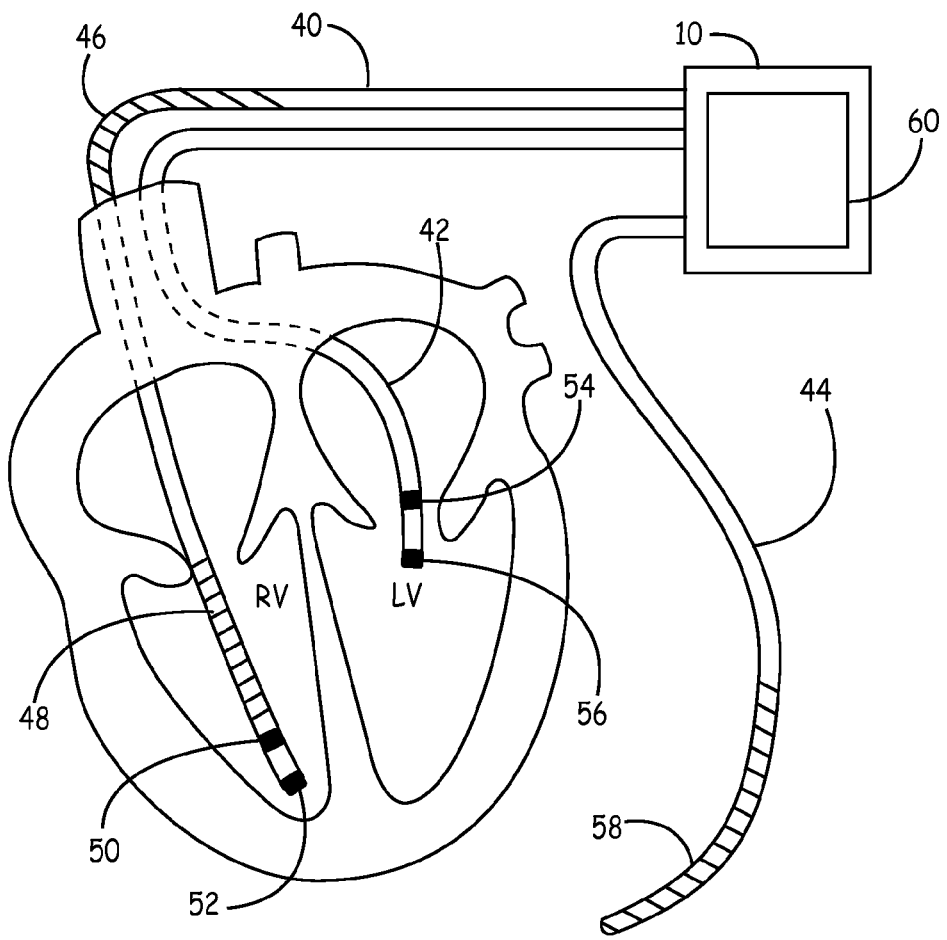
FIG. 2 illustrates one IMD configuration for acquiring EGM data in a TWA assessment method.

FIG. 2 illustrates one IMD configuration for acquiring EGM data in a TWA assessment method. IMD 10 may be embodied as any of a number of IMDs, such as a cardiac monitoring device, a pacemaker, an implantable cardioverter defibrillator, a neurostimulator, or a drug delivery device. EGM data suitable for assessing TWA may be acquired from signals sensed by subcutaneous electrodes, epicardial electrodes, transvenous or endocardial electrodes, or a neurostimulation lead. In one embodiment, multiple sensing vectors are selected for acquiring EGM data for TWA assessment. A number of possible sensing vectors may be selected from any combination of available electrodes.

In the example shown in FIG. 2, IMD 10 is embodied as an implantable cardioverter defibrillator and is shown coupled to a set of leads configured for delivering pacing, cardioversion, and defibrillation pulses and sensing EGM signals for detecting and discriminating heart rhythms. IMD 10 is coupled to a right ventricular (RV) lead 40 carrying a superior vena cava (SVC) coil electrode 46 and an RV coil electrode 48 for use in delivering cardioversion and defibrillation shock pulses. RV lead 40 carries a tip electrode 52 and a ring electrode 50 used in pacing and sensing functions in the right ventricle.

IMD 10 is further coupled to a coronary sinus (CS) lead 42 equipped with a tip electrode 56 and ring electrode 54 for use in sensing and pacing functions in the left heart chambers. CS lead 42 may be advanced into a cardiac vein so as to position CS tip electrode 56 and ring electrode 54 in a desired location over the left ventricle.

IMD 10 is provided with a can or case electrode 60 that may be used in combination with any of the cardiac electrodes for delivering stimulation pulses or sensing cardiac electrical signals in a unipolar mode. IMD 10 may be coupled to one or more subcutaneous leads 44 carrying a subcutaneous electrode 58, which may be a coil, patch or other type of electrode used in combination with SVC coil electrode 46, RV coil electrode 48, and/or can electrode 60 for delivering cardioversion or defibrillation shock pulses. Subcutaneous electrode 58 may alternatively be used in combination with any of the tip or ring electrodes 50, 52, 54 and 56 for sensing or pacing in unipolar modes.

Numerous different sensing vectors may be selected from the electrodes available in the system shown in FIG. 2. Any electrode located on RV lead 40 or CS lead 42 may be selected in a unipolar sensing combination with can electrode 60 or subcutaneous electrode 58. Any combination of two electrodes located on RV lead 40 or CS lead 42 may be selected for bipolar sensing. Both far-field and near-field EGM signals can used for TWA assessment. Embodiments are not limited to the lead and electrode arrangement shown in FIG. 2. Numerous variations exist in the types of leads and electrodes that may be included in a system for monitoring TWA.

Methods described herein are not limited to implementation in an implantable medical device system. Assessment of TWA according to methods described below may be implemented in external medical device systems acquiring ECG signals from an ambulatory or bedside monitor.

Figure 3:
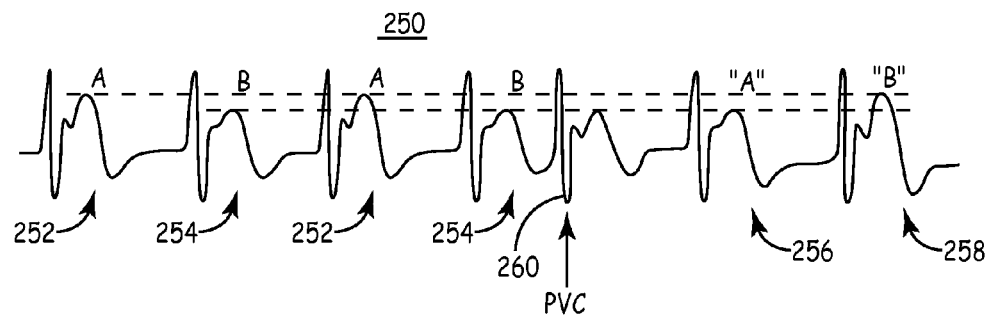
FIG. 3 is an illustration of TWA phase reversal associated with a premature ventricular contraction (PVC).

FIG. 3 is an illustration of TWA phase reversal associated with a premature ventricular contraction (PVC). An EGM recording 250 is shown including T-wave signals with A-B-A-B labeling of consecutive "A" T-waves 252 and "B" T-waves 254 occurring prior to a PVC 260. A PVC 260 occurs. The T-wave associated with the PVC is ignored for the purposes of TWA assessment. The first T-wave 256 during the first normal beat following PVC 260 is labeled "A" consistent with the A-B-A-B labeling pattern established prior to the PVC 260. The amplitude and morphology of T-wave 256, however, more closely match the "B" T-waves 254 occurring prior to PVC 260, not the pre-PVC "A" T-waves 252. Likewise, the next "B" T-wave 258 occurring after the PVC 260 can be seen to be similar in amplitude and morphology to the "A" T-waves 252 prior to the PVC 260. This reversal of the A-B morphology during TWA is referred to herein as "phase reversal" and is thought to be an indicator of increased risk for ventricular arrhythmias.

Figure 4:
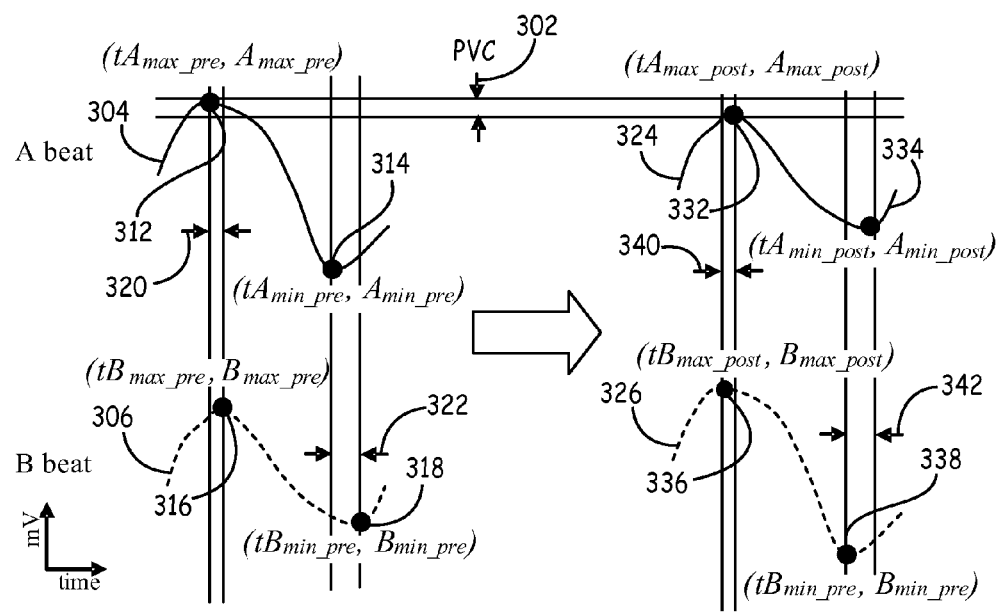
FIG. 4 is a diagram of "A" and "B" T-waves occurring prior to a PVC and after a PVC.

FIG. 4 is a diagram of "A" and "B" T-waves occurring prior to a PVC and after a PVC. T-waves 304 and 306 occur prior to a PVC 302. T-waves 304 and 306 are consecutive T-waves and are shown one above the other in order to highlight timing differences corresponding to maximum and minimum T-wave amplitudes. The consecutive T-waves 304 and 306 are labeled as "A" and "B" beats for the purpose of computing differences in T-wave features from beat-to-beat for detecting TWA.

The "A" T-wave 304 is characterized by a maximum amplitude ($A_{max}$) 312 occurring at a time $tA_{max\_pre}$ and a minimum amplitude ($A_{min}$) 314 occuring at a time $tA_{min\text{-}pre}$. The "B" T-wave 306 is characterized by a maximum amplitude ($B_{max}$) 316 occurring at a time $tB_{max\_pre}$ and a minimum amplitude ($B_{min}$) 318 occurring at a time $tB_{min\_pre}$. Maximum amplitude time difference 320 between $tA_{max\_pre}$ and $tB_{max\_pre}$ is shown. The minimum amplitude time difference 322 between $tA_{min\text{-}pre}$ and $tB_{min\_pre}$ is also shown.

The maximum amplitude time difference 320, the minimum amplitude time difference 322, the amplitude difference between the maximum "A" and maximum "B" amplitudes 312 and 316, or the difference between the minimum "A" and "B" amplitudes 314 and 318, or any combination thereof, may be used to detect TWA. It is contemplated that other features of the T-waves 304 and 306, such as maximum slope, time of maximum slope, time of minimum slope, T-wave width, T-wave area, or the like, may be used to assess morphological differences between consecutive T-waves for the detection of TWA and for detection of TWA phase reversal.

A PVC 302 is detected during TWA. In some embodiments, TWA assessment may be taking place when a PVC 302 occurs. In other embodiments, T-wave signal data may be acquired, stored, and then analyzed retrospectively if a PVC 302 is detected. PVC 302 may be a spontaneous PVC or induced by a pacing pulse delivered to test for the occurrence of TWA phase reversal.

When the T-wave signals continue to be consecutively labeled with the A-B-A-B convention, applied to the post-PVC beats 324 and 326, the post-PVC "A" beat 324 more closely matches the pre-PVC "B" beat and vice versa. In other words, the post-PVC "A" T-wave maximum amplitude 332 and corresponding time $tA_{max\_post}$ will approximately match the pre-PVC "B" T-wave maximum amplitude 316 and corresponding time $tA_{max\text{-}post}$. The post-PVC "B" T-wave maximum amplitude 336 and corresponding time $tB_{max\text{-}post}$ will more closely match the pre-PVC "A" T-wave maximum amplitude 312 and corresponding time $tA_{max\text{-}pre}$, and so on.

As a result of phase reversal, the difference between a post-PVC "A" T-wave feature and a post-PVC "B" T-wave feature will be opposite in sign as compared to the pre-PVC difference. This change in sign or polarity of the "A" minus "B" beat features can be observed by examining the post-PVC T-wave features as compared to the respective pre-PVC T-wave features. For example, prior to the PVC 302, the "A" maximum amplitude 312 and minimum amplitude 314 occur at time points earlier than the "B" maximum amplitude 316 and minimum amplitude 318, resulting in positive time differences 320 and 322 between the "A" and "B" beats. Subsequent to the PVC 302, the "B" maximum amplitude 336 and minimum amplitude 338 occur earlier than the "A" maximum amplitude 332 and minimum amplitude 334, resulting in negative time differences 340 and 342 between the "A" and "B" beats.

Figure 5:
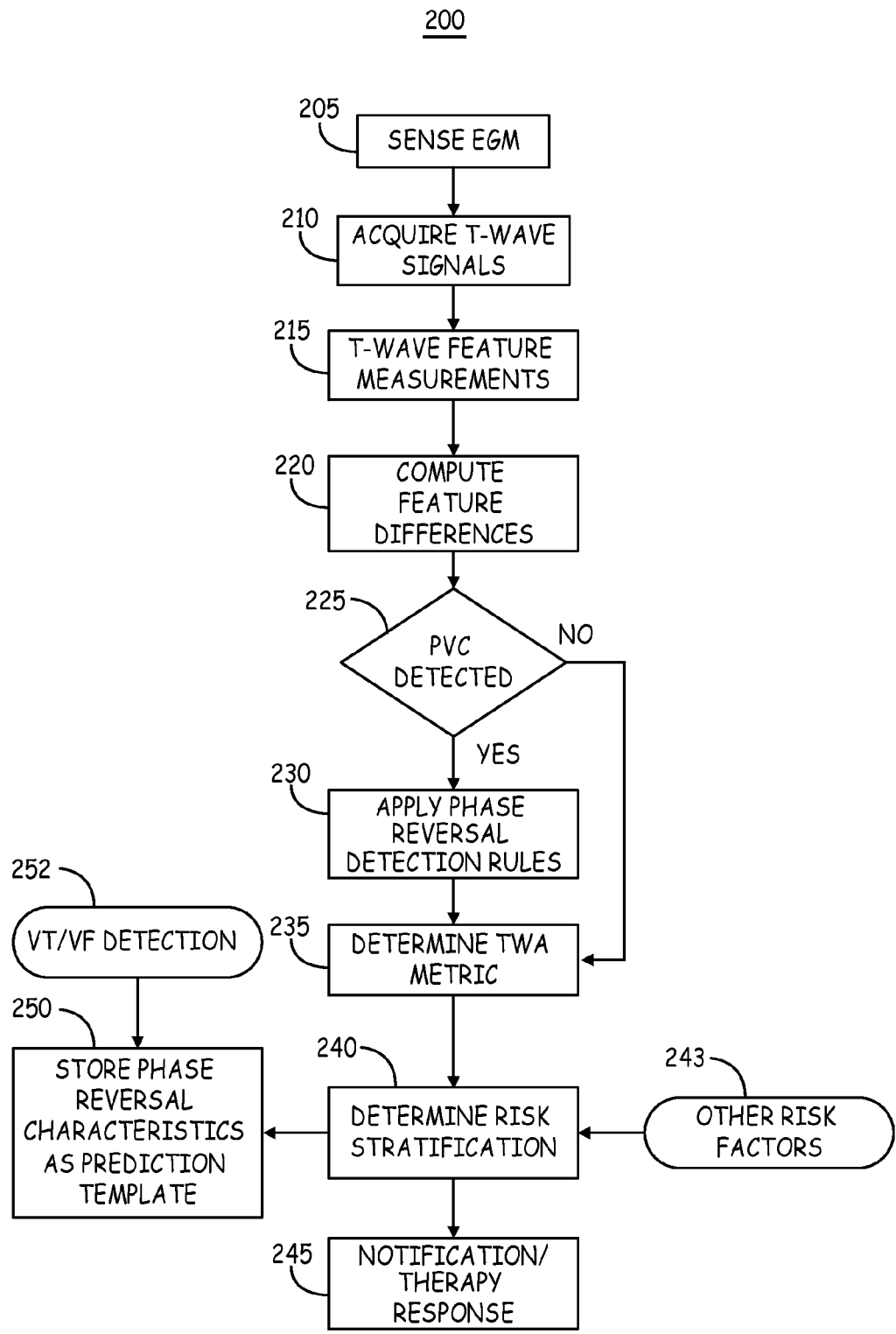
FIG. 5 is a flow chart summarizing a method for assessing TWA according to one embodiment for classifying a patient's risk for arrhythmia.

FIG. 5 is a flow chart summarizing a method for assessing TWA according to one embodiment. Flow chart 200 is intended to illustrate the functional operation of a medical device system, and should not be construed as reflective of a specific form of software or hardware necessary to practice the methods described herein. It is believed that the particular form of software will be determined primarily by the particular system architecture employed in the device and by the particular detection and therapy delivery methodologies employed by the device. Providing software to accomplish the methods described in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Method 200 for assessing TWA includes sensing an EGM signal at block 205. T-wave signals are acquired by the IMD at block 210 during a T-wave sensing window set in response to sensed R-waves. Typically, a T-wave sensing window is set relative to detected R-waves for acquiring and storing a plurality of consecutive T-wave signals, for example 10 to 20 T-wave signals. Methods for acquiring T-wave signals are generally described in commonly-assigned U.S. Pat. Pub. No. 2006/0116592 (Zhou, et al.), incorporated herein by reference in its entirety.

At block 215, T-wave measurements are performed on the acquired T-wave signals. T-wave measurements may include detecting any feature of the T-wave signal known to alternate during a TWA episode. Examples of the T-wave measurements that may be made are T-wave maximum amplitude, T-wave minimum amplitude, maximum-to-minimum (peak-to-peak) amplitude difference, T-wave area (integral), T-wave maximum slope, T-wave minimum slope, and time points corresponding to T-wave minimum amplitude and/or T-wave maximum amplitude. The features determined from each T-wave signal may be stored in a T-wave matrix in which T-waves are assigned an A or B label in an alternating manner as generally disclosed in U.S. Patent Publication No. 2006/0116596 (Zhou, et al.), hereby incorporated herein by reference in its entirety.

At block 220, differences between corresponding T-wave features of "A" and "B" T-wave signals are computed. These differences may be used at block 235 for computing a TWA metric. If a PVC is detected at block 225, phase reversal detection rules are applied at block 230 to determine if a reversal in the A-B pattern of TWA has occurred. The reversal of the T-wave morphology or features defining an A-B pattern occurring prior to a PVC to a "B-A" pattern occurring after a PVC may indicate a higher risk of arrhythmias, and this phase reversal may be included in an assessment of TWA for determining arrhythmia risk.

A PVC detected at block 225 may be a premature pacing pulse or a spontaneously occurring intrinsic PVC. A clinician may initiate a TWA assessment using a programmer or other external device. The TWA assessment performed may include measuring TWA over a series of cardiac cycles as indicated by blocks 205 through 220, then delivering a premature ventricular pacing pulse at block 225 and applying phase reversal detection rules at block 230 to determine if a phase reversal has occurred.

Alternatively, the IMD may automatically deliver a premature ventricular pacing pulse when TWA is detected to determine if phase reversal occurs in response to the pacing-induced PVC. Additionally or alternatively, the IMD may monitor for PVCs and when a spontaneous PVC is detected, the rules for detecting phase reversal are applied at block 230. A PVC is generally detected when two ventricular events occur without an intervening atrial event.

At block 230, differences between A and B T-waves occurring before and after the T-wave are analyzed to determine if a phase reversal has occurred. In one embodiment, the pre-PVC and post-PVC maximum amplitude differences, minimum amplitude differences, and time differential between the maximum amplitudes and the time differential between the minimum amplitudes are analyzed. Any morphology features of the S-T segment of the EGM signal, including amplitudes, timing differences, slopes and areas, may be used in detecting TWA phase reversal.

In one embodiment, the following equations may be applied at block 230 in Boolean logic format:

IF $(A_{max\_pre}-B_{max\_pre})*(A_{max\_post}-B_{max\_post})<0$

OR $(A_{min\_pre}-B_{min\_pre})*(A_{min\_post}-B_{min\_post})<0$

OR $(tA_{max\_pre}-tB_{max\_pre})*(tA_{max\_post}-tB_{max\_post})<0$

OR $(tA_{min\_pre}-tB_{min\_pre})*(tA_{min\_post}-tB_{min\_post})<0$

THEN

Phase_reversal=TRUE

ELSE

Phase reversal=FALSE

ENDIF

If any one of the T-wave features is reversed in phase, the product of the A-B feature difference prior to the PVC (pre) and the A-B feature difference after the PVC (post) will be a negative value, i.e. less than zero. In this example, if any one of the T-wave features is reversed in phase such that at least one of the products listed above results in a negative value, TWA phase reversal is detected using the OR logic indicated. If none of the products of the pre- and post-PVC T-wave feature differences are negative, TWA phase reversal is not detected. In other embodiments, two or more T-wave features may be required to exhibit phase reversal before phase reversal is detected.

Any combination of weighted products or differences of pre- and post-PVC A-B T-wave feature differences may be used in a rule or set of rules applied for detecting T-wave phase reversal. Some A-B T-wave differences may have greater predictive power of phase reversal than other T-wave feature differences between A and B beats. As such, some differences may be given greater weight in detecting phase reversal than other differences.

The differences between A and B beats, both prior to the PVC and after the PVC, may be required to reach a predefined threshold in order to verify the presence of TWA before and after the PVC. Additionally, the sum of the pre- and post-PVC differences may be required to be approximately zero or within some limited range to confirm phase reversal of similar morphologies. For example, the maximum amplitude difference between A and B beats before the PVC and the maximum amplitude difference between A and B beats after the PVC may be required to be approximately equal in magnitude (and opposite in sign) before detecting phase reversal as indicated by the following equation:

$(A_{max\_pre}-B_{max\_pre})+(A_{max\_post}-B_{max\_post})<\pm\text{phase reversal threshold}$ where the phase reversal threshold may be defined as a range of values centered on zero (including positive and negative values) corresponding to acceptable variation in the measurement of the A and B beat T-wave features.

As described in the previously-incorporated '592 published application, the T-wave measurements may be evaluated for possible contamination due to artifacts or signal noise. This evaluation may be based on the differences between "A" and "B" T-wave measurements occurring in the T-wave signals. If TWA is present, the differences in the "A" and "B" T-wave measurements will be consistent in phase before or after a PVC, evidencing an A-B-A-B-A-B pattern. For example, if T-wave amplitudes are measured before a PVC is detected, the "A" T-wave amplitudes will either be greater than the "B" T-wave amplitudes most of the time or less than the "B" T-wave amplitudes most of the time.

In detecting TWA phase reversal, the last two T-waves immediately preceding the PVC and the T-waves of the first two beats immediately following the PVC may be used to compute the pre- and post-PVC T-wave differences. Alternatively, multiple A-B pairs preceding the PVC and multiple A-B pairs subsequent to the PVC may be used to detect TWA phase reversal. Any number of T-waves may be used in computing A-B feature differences pre- and post-PVC for detecting phase reversal.

Furthermore, it is recognized that other events may occur which trigger a TWA phase reversal or a TWA phase reversal might occur spontaneously. While embodiments described herein refer to a PVC as the event associated with TWA phase reversal, the methods described herein for detecting TWA phase reversal may be used when other events or causes associated with TWA phase reversal occur.

At block 235, a TWA metric is determined. The TWA metric may take into account a measure of A-B T-wave differences as well as the presence of phase reversal. At block 240, the patient's arrhythmia risk stratification is determined based on the TWA metric. The TWA metric may be compared to criteria set for identifying arrhythmia risk, which may include multiple threshold levels or different sets of criteria for differentiating between low, medium and high risk levels. For example, a patient having TWA and phase reversal may be classified as high risk. A patient having TWA and no phase reversal may be classified as moderate risk. A patient having no TWA and no phase reversal may be classified as low risk. In some cases, the TWA metric may be based on the presence of TWA phase reversal alone.

Other arrhythmia risk factors may be considered for determining a patient's arrhythmia risk stratification at block 240. Other markers of arrhythmia risk (block 243), such as non-sustained VT occurrence or number of PVCs per hour, may be provided as input to block 240, for use in determining a patient's arrhythmia risk. Based on the patient's arrhythmia risk, a patient or clinician notification may be automatically generated at block 245. Additionally or alternatively, the IMD may respond to an increased arrhythmia risk by initiating or adjusting a therapy. Arrhythmia prevention therapy may be delivered, for example in the form of pacing, neurostimulation, or drug delivery. More aggressive arrhythmia detection criteria may be set to allow quicker detection of an arrhythmia, e.g. requiring fewer R-R intervals meeting a tachycardia or fibrillation interval to detect a corresponding arrhythmia.

TWA characteristics, including the phase reversal characteristics, may be stored in a template at block 250, along with the occurrence of detected arrhythmias, for use in predicting future arrhythmias. For example, if VT or VF episodes are detected at block 252, the TWA characteristics leading up to the VT/VF episode may be stored as a prediction template such that when the same TWA pattern is detected in the future, an alert may be generated or more aggressive detection and therapy delivery options may be taken.

Thus, a system and method for assessing TWA have been presented in the foregoing description with reference to specific embodiments. It is appreciated that various modifications to the referenced embodiments may be made without departing from the scope of the disclosure as set forth in the following claims.

The invention claimed is:

1. A medical device system for classifying a patient's risk for arrhythmias, comprising:
    an electrode to sense a cardiac electrogram (EGM) signal comprising a plurality of T-wave signals;
    sensing circuitry coupled to the electrode to receive and filter the EGM signal; and
    a processor coupled to the sensing circuitry and configured to:
        select a first pair of T-wave signals from the plurality of T-wave signals, the selected first pair comprising a first T-wave signal and a second T-wave signal, the second T-wave signal occurring consecutively after the first T-wave signal,
        determine a feature of the first T-wave signal and a feature of the second T-wave signal,
        compute a first difference between the feature of the first T-wave signal and the feature of the second T-wave signal,
        select a second pair of T-wave signals occurring after the first pair of T-wave signals, the selected second pair comprising a third T-wave signal and a fourth T-wave signal, the fourth T-wave signal occurring consecutively after the third T-wave signal,
        determine a feature of the third T-wave signal and a feature of the fourth T-wave signal,
        determine a second difference between the feature of the third T-wave signal and the feature of the fourth T-wave signal,
        compare the first difference and the second difference,
        detect a T-wave alternans phase reversal of a T-wave morphology from an A-B order to a B-A order in response to comparing the first difference and the second difference, and
        classify the patient's arrhythmia risk in response to detecting the phase reversal.

2. The system of claim 1 wherein determining the first difference and the second difference comprises one of determining an amplitude difference and a time difference.

3. The system of claim 1 wherein the processor is further configured to detect a spontaneous premature ventricular contraction, wherein the first pair of T-wave signals occurs prior to the premature ventricular contraction and the second pair of T-wave signals occurs subsequent to the premature ventricular contraction.

4. The system of claim 1 further comprising a pulse generator coupled to the electrode and control circuitry for controlling the pulse generator to deliver a premature pacing pulse, wherein the first pair of T-wave signals occurs prior to the premature pacing pulse and the second pair of T-wave signals occurs subsequent to the premature pacing pulse.

5. The system of claim 1 wherein comparing the first difference and the second difference comprises computing a product of the first difference and the second difference, and wherein the processor is configured to detect the T-wave alternans phase reversal when the product is less than zero.

6. The system of claim 1 wherein the processor is further configured to comparing the first difference and the second difference to a threshold, and wherein detecting the T-wave alternans phase reversal comprises verifying that the first difference and the second difference each exceed the threshold.

7. The system of claim 1 wherein comparing the first difference and the second difference comprises computing sum of the first difference and the second difference, and wherein detecting the T-wave alternans phase reversal comprises verifying that the sum of the first difference and the second difference is within a predetermined range.

8. The system of claim 1 wherein the processor is further configured to compute a metric of T-wave alternans in response to detecting the phase reversal, compare the metric to an arrhythmia risk threshold, and generate a notification of arrhythmia risk in response to the comparison.

9. The system of claim 1 further comprising a therapy delivery module coupled to the processor, wherein the processor is further configured to detect an arrhythmia in response to the EGM signal, and adjust one of an arrhythmia prevention therapy and an arrhythmia detection criterion in response to detecting the phase reversal.

* * * * *